United States Patent [19]

Le Grouyellec et al.

[11] 4,329,318

[45] May 11, 1982

[54] CAPSULES FOR DETERMINING THE ALCOHOL CONTENT OF THE BREATH

[76] Inventors: André Le Grouyellec, Le Vialgoët, 56390 Brandivy; Jacques Ponsy, Kerbois, 56400 Auray, both of France

[21] Appl. No.: 75,276

[22] Filed: Sep. 13, 1979

[30] Foreign Application Priority Data

Sep. 14, 1978 [FR] France ................................ 78 26879

[51] Int. Cl.³ ........................ G01N 1/22; G01N 1/48
[52] U.S. Cl. .................................... 422/59; 422/84; 422/85; 422/220; 55/418; 55/274
[58] Field of Search ..................... 23/232 R, 230 M; 422/58, 59, 60, 61, 84, 85, 102, 83, 176, 220; 73/23; 55/274, 275, 418; 128/719

[56] References Cited

U.S. PATENT DOCUMENTS

| Re. 27,008 | 6/1966 | Luckey | 422/85 |
|---|---|---|---|
| 2,097,650 | 11/1937 | Stampe | 422/88 |
| 3,018,847 | 1/1962 | Gerlich | 55/418 |
| 3,388,975 | 6/1968 | Wallace | 422/86 |
| 3,459,508 | 8/1969 | Miczka | 422/85 |
| 4,178,919 | 12/1979 | Hall | 422/84 |

Primary Examiner—William F. Smith
Assistant Examiner—Chris Konkol
Attorney, Agent, or Firm—Laff, Whitesel, Conte & Saret

[57] ABSTRACT

A capsule for testing the alcohol content in human breath contains a solid reagent. The capsule is capable of passing a gaseous fluid or liquid in a predetermined quantity for reacting with the reagent. The capsule has a middle part which is almost cylindrical and at least at one end has an orifice for regulating the fluid entering through the orifice and distributing it into the reagent.

9 Claims, 11 Drawing Figures

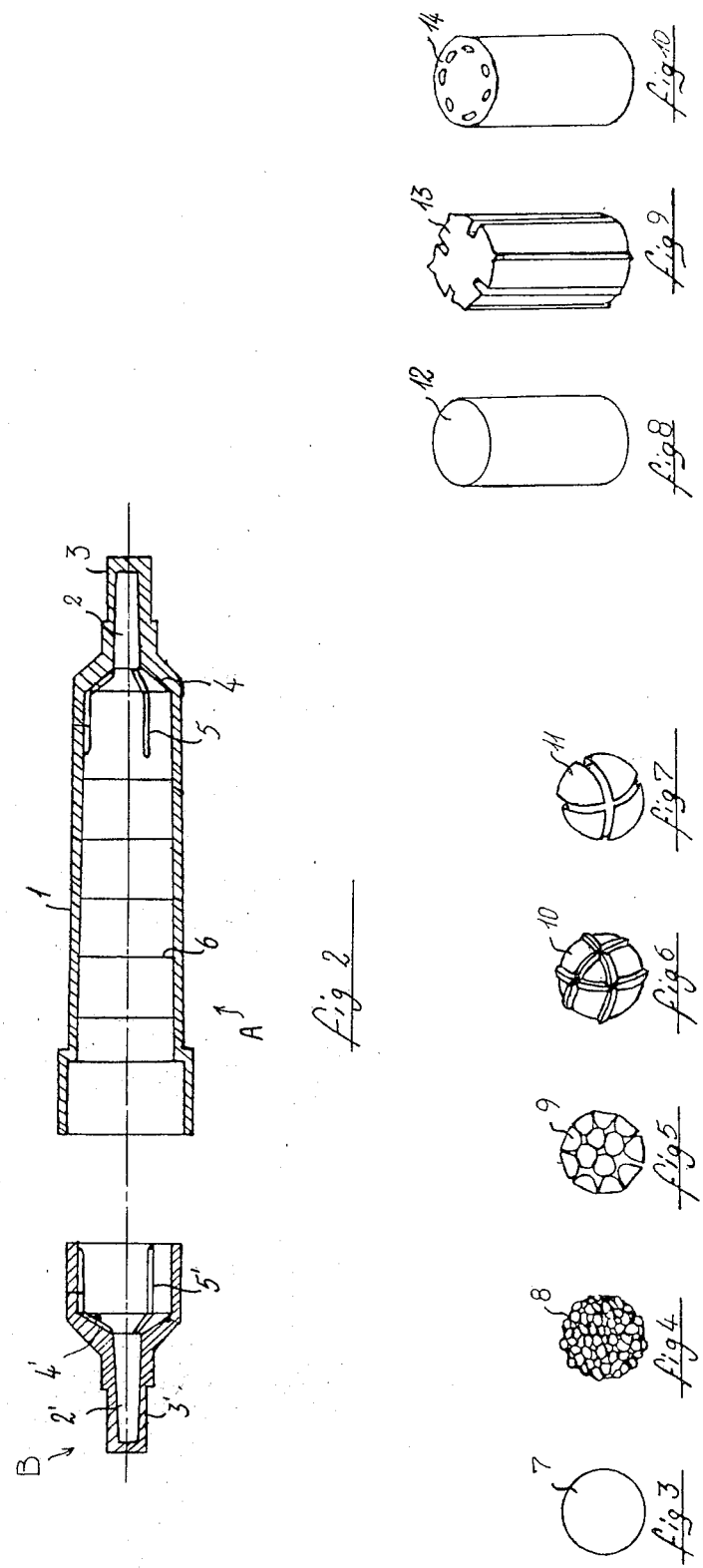

CAPSULES FOR DETERMINING THE ALCOHOL CONTENT OF THE BREATH

The present invention concerns gas or liquid test capsules and more particularly test capsules of the alcohol test type intended for determining the alcohol content of the gases exhaled from the lungs.

Up until now these capsules have been made as sealed glass ampoules containing a reagent, but these are very expensive and not of very rapid manufacture.

One object of the invention comprises of providing a gas or liquid test capsule manufactured from parts moulded in plastics material, the moulds of which enable a rapid and automated manufacture, from a minimum number of parts. The reagent may be a chemical compound or a combination of chemical reagents.

According to one aspect of the invention, a test capsule of the alcohol test type contains a solid reagent. The capsule is capable of being passed through by a gaseous fluid or liquid in predetermined quantity for reacting with the reagent. The capsule has, in its middle part, an almost cylindrical portion. At least at one end of the capsule has an orifice connecting with the almost cylindrical portion by a ball-like surface forming a somewhat valve-like seat. The regulating element ensures the correct distribution of the fluid entering through the orifice, into the reagent.

The feature of the invention mentioned above as well as others will appear more clearly on reading the following description of embodiments, the description being made in relation to the attached drawings among which:

FIG. 2 is an exploded view, in cross section, of the covering of the capsule of FIG. 1;

FIGS. 3 to 7 are views of various spherical embodiments of regulating elements usable in the capsule of FIG. 1;

FIGS. 8 to 10 are views of other cylindrical variants of regulating elements.

Figure 1:
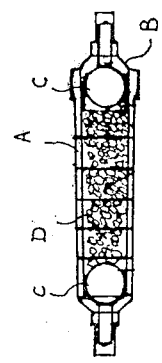
FIG. 1 is a diagrammatic view, in cross section, of a test capsule according to the invention.

The capsule of FIG. 1 is composed of a body A, a plugging cap B, two regulating elements C and a dose or measured quantity of reagent D.

The body A, FIG. 2, is composed of cylinder 1 blocked at one end by a reduction in diameter defining in orifice 2 more or less calibrated according to the requirements demanded.

The body A has, towards the end blocked initially by an end piece 3, a seating 4 having three or more ribs 5, the ribs extending to a predetermined height or distance into the bore of the cylindrical part of the body A. These ribs are in contact with a regulating element C, FIG. 1. They have the effect of controlling the centering of this regulating element as well as insuring the distribution or passage of the gas or liquid introduced through the orifice 2.

Furthermore, the body A has in the zone containing reagent D peripheral marks 6 permitting the taking of readings in use of the capsule.

The plugging cap B, FIG. 2, is fitted into in the body A by an inner or outer skirting and has a seating and an end completely identical in its construction with the blocked end of the body A, that is to say, having an orifice 2, and end piece 3', a seating 4' and ribs 5'.

The body A and the plugging cap B are preferably made of a transparent, translucent or slightly tinted plastics material according to the effect sought and the compatability of the plastics material and the reagent.

The assembly—body A and cap B—ensures, after welding or gluing together of the two parts, an imperviousness to exchanges with the environment outside. The assembly is practically inviolable except by cutting or breaking off the end pieces 2 and 2' at the time of use.

The regulating elements C are made of plastics material and may, according to requirements, be in several forms, as for example, those shown in FIGS. 3 to 10.

The regulating element 7 of FIG. 3 is spherical and smooth and, while modulating the passage of the gas or liquid through the mass of the reagent, gives a passage distribution which is not a very good laminar flow.

The element 8 of FIG. 4 is spherical with asperities which permit its centering in a body not having ribs. These asperities create a turbulence greater than that created by the element 7 and, therefore, a more substantial penetration into the mass of the reagent D.

The element 9 of FIG. 5 is spherical with facets and in the middle of the body, it is somewhat like the element 8. These facets create a turbulence greater than that created by the element 8.

The elements 10 and 11 of FIGS. 6 and 7 are spherical with circular ribs extending in all directions the significance of which is a function of the output of the gas or liquid investigated. These ribs may be exterior (FIG. 6) or interior (FIG. 7). The centering of this regulating element in the body is effected either by the projecting ribs of the sphere or by the ribs 5 of the body. The embodiments 10,11 of FIGS. 6 and 7 produce diffusion of the gas or of the liquid in the mass of the reagent which is more substantial than for the elements 7, 8 or 9.

The elements 12, 13 and 14 of FIGS. 8, 9 and 10 are cylindrical regulating elements, the height of which is greater than the diameter so as to ensure the automatic distribution of gas or liquid without risk of wrongly positioning the body.

The element 12, FIG. 8 is smooth with a centering similar to the centering of the element 7. It ensures a very good laminar flow distribution of the current of gas or liquid into the mass of the reagent.

The element 13 has longitudinal scores or slits with a centering rib with a function similar to that of the element 8. It ensures a laminar flow distribution of the current of gas or liquid with a better channelling than with the element 12.

The element 14, FIG. 10 is perforated longitudinally. The current of gas or liquid is controlled by the diameter, the positions and the number of the perforations. The centering is similar to that of the element 7.

These elements permit the gas or the liquid which is to be tested to pass into the mass D of the reagent by guiding it towards the inside or the outside according to the passage conditions in the reagent.

The regulating elements may be coloured to indicate to the user the direction of the passage of the gas or liquid.

Figure 11:
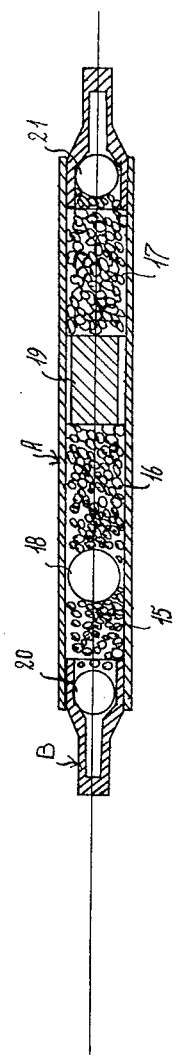
FIG. 11 is a diagrammatic view of a variant of the test capsule of FIG. 1.

In the preceding description, the basic components of a test capsule of simplified form have been considered. FIG. 11 shows a more complex test capsule with several possible reagent stages 15, 16 and 17, possibly different from one another, and separated by regulating elements 18 and 19 of different shapes, the end elements being indicated at 20 and 21. In this variant, between each dose or measured quantity of reagent 15, 16, 17 is a regulating element. These elements may be of different shapes. Suitable distributions of current are obtained according to the effects to be investigated by the dose in each reagent.

The body A and the plugging cap B are sealed together, as by gluing, welding, ultra sonics or any other suitable method, thereby ensuring a perfect imperviousness of the whole capsule. The checking of the imperviousness may be effected by placing test capsules in an enclosure where, first of all, a vacuum is created and then a gas or a liquid is introduced which is capable of reacting with the compound or compounds of the reagent or reagents. For example alcohol will be introduced for an alcohol test.

The cutting or breaking of the end pieces 3, 3' permits these test capsules to be put into use.

Of course a plugging cap may be provided (such as cap B) at each end of a cylindrical body. The capsule is then composed of three parts.

I claim:

1. A self contained test capsule of the alcohol test type containing a solid reagent, fluid flow regulating means, the capsule being capable of being passed through by a gaseous fluid or liquid distributed by said regulating means in a predetermined quantity for reacting with the said reagent, the capsule having in its middle part an almost cylindrical portion, one end of said capsule having an orifice in communication with the almost cylindrical portion by a surface forming a seating for a fluid flow regulating element, the surface of the said seating having ribs for ensuring a centering of the regulating element at a position on the axis of the capsule, said seating positioning said regulating element to ensure a distribution of the fluid entering through the orifice into the reagent.

2. A capsule according to claim 1, characterized in that the regulating element is spherical.

3. A capsule according to claim 1, characterized in that said spherical regulating element has a smooth surface.

4. A capsule according to claim 1, characterized in that said regulating element has a spherical surface with facets.

5. A capsule according to one of the claims 1 to 4 characterized in that each end of the capsule has an orifice of small diameter with a seating associated with a regulating element.

6. A capsule according to one of the claims 1 to 4 characterized in that a plurality of regulating elements are provided at predetermined places along the almost cylindrical part of the capsule.

7. A capsule according to claim 5, characterized in that a plurality of regulating elements are provided at predetermined places along the almost cylindrical part of the capsule.

8. A capsule according to claim 5, characterized in that the enclosure of the capsule is formed by said almost cylindrical body having said seating and orifice and a cap, another orifice and another seating on the body, said cap and body being made hermetically integral.

9. A capsule according to claim 6, characterized in that the enclosure of the capsule is formed by said almost cylindrical body having said seating and orifice and a cap, another orifice and another seating on the body, said cap and body being made hermetically integral.

* * * * *